United States Patent [19]

Williams, Jr.

[11] Patent Number: 4,533,744
[45] Date of Patent: Aug. 6, 1985

[54] HYDROSILYLATION METHOD, CATALYST AND METHOD FOR MAKING

[75] Inventor: Robert E. Williams, Jr., Scotia, N.Y.

[73] Assignee: General Electric Company, Schenectady, N.Y.

[21] Appl. No.: 670,250

[22] Filed: Nov. 13, 1984

Related U.S. Application Data

[62] Division of Ser. No. 527,538, Aug. 29, 1983, Pat. No. 4,503,160.

[51] Int. Cl.$^3$ ............................ C07F 7/08; C07F 7/18
[52] U.S. Cl. .................................................... 556/479
[58] Field of Search ........................................ 556/479

[56] References Cited

U.S. PATENT DOCUMENTS

| | | | |
|---|---|---|---|
| 3,419,593 | 12/1968 | Willing | 556/479 |
| 3,715,334 | 2/1973 | Karstedt | 556/479 X |
| 3,907,852 | 9/1975 | Oswald et al. | 556/479 X |

*Primary Examiner*—Paul F. Shaver
*Attorney, Agent, or Firm*—William A. Teoli; James C. Davis, Jr.; James Magee, Jr.

[57] ABSTRACT

A hydrosilation catalyst is provided having platinum atoms anchored onto a hydroxylated oxide of silicon or aluminum by Pt—S linkages through sulfur organo siloxy groups. A hydrosilation method and a method for making such platinum catalyst is also provided.

6 Claims, No Drawings

HYDROSILYLATION METHOD, CATALYST AND METHOD FOR MAKING

This application is a division of application Ser. No. 527,538, filed Aug. 29, 1983, now U.S. Pat. No. 4,503,160.

BACKGROUND OF THE INVENTION

The present invention relates to a hydrosilylation method using a hydroxylated oxide of silicon or aluminum having chemically combined platinum atoms. More particularly, the present invention relates to a platinum catalyst having platinum atoms anchored onto the surface of a hydroxylated oxide of silicon or aluminum through platinum sulfur linkages.

Prior to the present invention hydrosilylation reactions, that is a reaction between silicon hydride and aliphatically unsaturated organic material to produce a silicon-carbon bond, were generally performed in the presence of an unsupported platinum catalyst such as Speier et al, J. Am. Chem. Soc., 1957, 79, 974, or Karstedt, U.S. Pat. Nos. 3,715,334 and 3,775,452, assigned to the same assignee as the present invention. Although valuable hydrosilylation results were often achieved using such unsupported platinum catalyst, it was difficult to recover platinum values upon completion of the hydrosilylation reaction. In addition, the platinum catalyst could not be reused after the reaction, as the platinum was generally in the form of the free metal which was catalytically less reactive and difficult to salvage.

As reported by Capka et al, Hydrosilylation Catalyzed by Transition Metal Complexes Coordinately Bound to Inorganic Supports, Institute of Chemical Process Fundamentals, Czechoslovak Academy of Sciences, Collection Czechoslov. Chem. Commun. (Vol. 39, 1974, pages 154–166), transition metal complexes bound to inorganic materials provide many advantages over unsupported catalysts of the prior art. It is further reported by Z.M. Michalska, Catalytic Activity of Supported Rhodium(I) and Platinum(0) Complexes in Hydrosilylation, J. of Molecular Catalysis, 3 (1977/78) 125-134, that improved catalyst performance can be achieved in olefin hydrosilylation reactions using certain complexes, for example, chloro-tris(triphenylphosphine)rhodium(I) or tetra-kis(triphenylphosphine)-platinum(0) attached to the surface of a silica support containing bound diphenylphosphine groups via a ligand exchange reaction. A catalyzed oxidation of 1-hexene by dioxygen using a monomeric organosulfide-rhodium carbonyl complex chemically bound to silica gel is reported by Eric D. Nyberg et al, J. Am. Chem. Soc., 1981, 103, 496-498. Although improved results have been achieved in the art using various supported metallic catalysts as compared to results using such catalysts free of such support, continuous investigation is being made to further evaluate the effectiveness of various substrates and types of attachment of active transition metal atoms, such as platinum, to the supporting substrate.

The present invention is based on the discovery that improved performance can be achieved with a platinum catalyst in hydrosilylation reactions by utilizing as the platinum catalyst, a hydroxylated oxide of silicon or aluminum having platinum atoms anchored to the surface of the hydroxylated oxide of silicon or aluminum through siloxyorganosulfur bonds by platinum-sulfur linkages. More particularly, the platinum atoms can be anchored to the surface of the hydroxylated oxide of silicon or aluminum by platinum-sulfur linkages by

groups, where R is a divalent $C_{(2-13)}$ organo radical, attached to the hydroxylated silicon oxide or aluminum oxide surface by siloxane linkages. This result is quite surprising, because experience has shown that sulfur containing materials generally adversely affect the catalytic activity of the platinum catalyst in hydrosilylation reactions.

STATEMENT OF THE INVENTION

There is provided by the present invention, a hydrosilylation catalyst comprising a hydroxylated oxide of silicon or aluminum having a surface area of about 100 to 800 square meters per gram and 0.05% to 5% by weight of chemically combined platinum atoms, which hydroxylated oxide of silicon or aluminum is derivatized with a plurality of

groups attached to the surface hydroxylated oxide of silicon or aluminum by

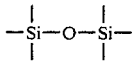

linkages, or

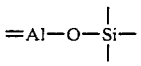

linkages, and the platinum atoms are chemically combined to the surface of the hydroxylated oxide of silicon or aluminum through the derivatized groups by Pt-S bonds.

There is also provided by the present invention, a hydrosilylation method which comprises effecting contact between a silicon hydride and an aliphatically unsaturated organic material in the presence of an effective amount of a platinum catalyst as previously defined.

In a further aspect of the present invention, there is provided a method for making a platinum catalyst comprising, (A) effecting reaction under conditions to provide the azeotropic removal of water and $C_{(1-8)}$ alkanol between a hydroxylated oxide of silicon or aluminum having a surface area of about 100 to about 800 square meters per gram and mercaptoorganoalkoxysilane of the formula, $$(R^1O)_3Si-R-SH, \qquad (1)$$

to produce a functionalized hydroxylated oxide of silicon or aluminum having a plurality of chemically combined mercapto organosiloxy groups attached to the surface of the hydroxylated oxide of silicon or aluminum by

linkages, or

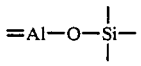

linkages, respectively, (B) drying the resulting functionalized oxide of silicon or aluminum of (A), (C) effecting reaction under substantially anhydrous conditions between the functionalized oxide of silicon or aluminum of (B) and a platinum halide where there is utilized sufficient platinum halide to provide 0.05% to 5% by weight of platinum based on the weight of functionalized oxide of silicon or aluminum, (D) recovering the resulting platinum catalyst from the mixture of (C).

where R is previously defined and $R^1$ is a $C_{(1-8)}$ alkyl radical.

Radicals included within R are, for example, alkylene radicals such as dimethylene, trimethylene, tetramethylene, pentamethylene, hexamethylene; arylene radicals such as phenylene, tolylene, xylylene; aralkylene radicals such as phenylenemethylene, phenyleneethylene, and halogenated derivatives of such radicals. Radicals included within $R^1$ are, for example, methyl, ethyl, propyl, butyl and pentyl.

Some of the inorganic oxides of silicon which can be used to make the platinum catalyst of the present invention, are for example, silica gel, fumed silica and glass. Preferably, silica gel is used which is further defined in Kirth Othmer Encyclopedia of Chemical Technology, 3rd Edition, Vol. 20, pages 773–775 (1982), John Wiley and Sons, New York.

There are included within the oxides of aluminum, materials such as alumina (all grades), for example, γ-alumina, and kieselguhr.

Among the mercaptans of formula (1) there are included,

γ-mercaptopropyltrimethoxysilane;
γ-mercaptopropyltriethoxysilane;
γ-mercaptopropyldimethoxymethylsilane;
γ-mercaptopropyldiethoxymethylsilane;

Some of the silicon hydrides which can be utilized in the practice of the hydrosilation method of the present invention are for example, organosilanes of the formula,

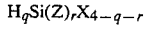

organocyclopolysiloxanes of the formula,

organopolysiloxane polymers of the formula,

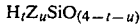

where X is a halogen radical, for example, chloro, Z is selected from monovalent hydrocarbon radicals, halogenated monovalent hydrocarbon and cyanoalkyl radicals, q is an integer equal to 1 or 2, r is a whole number equal to 0 to 3 inclusive, and the sum of q and r is equal to 1 to 4 inclusive, s is an integer equal to 3 to 18 inclusive, t has a value equal to 0.0001 to 1 inclusive, u has a value equal to 0 to 2.5 inclusive, and the sum of t and u is equal to 1 to 3 inclusive. Z is preferably methyl, a mixture of methyl and phenyl, or a mixture of methyl and vinyl.

The aliphatically unsaturated material which can be utilized in combination with the above described silicon hydride in the practice of the hydrosilation method of the present invention can contain olefinic or acetylenic unsaturated compounds known to the art. The aliphatically unsaturated materials can contain carbon and hydrogen only, or can contain carbon and hydrogen chemically combined with another element or elements. In instances where the aliphatic unsaturated material contains elements other than carbon and hydrogen, it is preferred that these elements be either oxygen, halogen, nitrogen, and silicon, or mixtures of these elements. The aliphatically unsaturated material can contain a single pair of carbon atoms linked by multiple bonds, or it can contain plurality of such aliphatically unsaturated bonds. As an illustration of the aliphatically unsaturated hydrocarbons which can be employed are for example, ethylene, propylene, butylene, octylene, styrene, butadiene, pentadiene, pentene-2, divinylbenzene, vinylacetylene, cyclohexene, etc. Higher molecular weight materials having at least 20 to 30 atoms also can be used, etc.

In addition to the above described aliphatically unsaturated hydrocarbons, there also can be included oxygen containing aliphatically unsaturated materials, such as methylvinylether, divinylether, phenylvinylether, monoallylether of ethylene glycol, allylaldehyde, phenylvinyl ketone, vinyl acetic acid, vinylacetate, linoleic acid, etc. Heterocyclic materials also are included, such as cyclohexene, cycloheptene, dihydrofuran, dihydropyrene, etc. Additional aliphatic unsaturated materials are, for example, acrylonitrile, allylcyanate, etc.

In the practice of the invention the platinum catalyst can be made by initially derivatizing the surface of a suitable hydroxylated oxide of silicon or aluminum, hereinafter "silicon oxide or silica gel" with an alkoxysilylorganomercaptan of formula (1), hereinafter "silylmercaptan". Reaction between the silica gel and the silyl mercaptan can be achieved by heating the ingredients, such as refluxing in a suitable inert organic solvent under an inert atmosphere, for example, nitrogen along with agitation of the mixture, such as stirring. The distillation can continue until there is no further water detectable as a result of the dehydration of the hydroxylated silica gel. The mixture can then be heated for an additional 8 to 48 hours under reflux conditions under an inert atmosphere. The mixture can then be allowed to cool to ambient temperatures and the suspended solids filtered under an inert atmosphere. The resulting solids can then be dried and analyzed if desired to determine the degree of attachment of the mercapto organosiloxy groups to the surface of the silicon oxide.

The derivatized silica gel then can be stirred with a substantially equal molar amount of platinum halides to provide for about 1 equivalent of mercaptan per gram atom of platinum under an inert atmosphere at ambient temperatures in the presence of an inert organic solvent, such as a $C_{(1-6)}$ alkanol. The resulting mixture can be agitated for 8 to 72 hours. The resulting mixture can then be filtered and the product can then be stored in a suitable moisture-free container.

Suitable platinum halides which can be used in making the platinum catalyst are for example, $H_2PtCl_6.nH_2O$ and metal salts, such as $NaHPtCl_6.(H_2O)n$, $KHPtCl_6.nH_2O$, $Na_2PtCl_6.H_2O$, $K_2PtCl_6.nH_2O$. Also, $PtCl_4.nH_2O$ and platinum type halides, such as $PtCl_2$, $Na_2PtCl_4.nH_2O$, $H_2PtCl_4.nH_2O$, $NaHPtCl_4.nH_2O$, $KHPtCl_4.nH_2O$, $K_2PtBr_4$.

Additional platinum halide complexed aliphatic hydrocarbon which can be used are taught by Speier in U.S. Pat. No. 2,823,218, by Ashby U.S. Pat. Nos. 3,159,601 and 3,159,662, for example, $[(CH_2=CH_2)]_2PtCl_2$; $(PtCl_2C_3H_6)_2)$, etc. Other platinum halides which can be utilized are shown by Lamoreaux U.S. Pat. No. 3,220,972, such as the reaction product of chloroplatinic acid hexahydrate and octyl alcohol, etc.

The hydrosilylation of suitable aliphatically unsaturated organic materials with silicon hydride can be achieved at temperatures in the range of from 0° C. to 200° C. There can be used sufficient platinum catalyst to provide for $10^{-4}\%$ to 1.0% by weight of platinum based on the weight of hydrosilylation reaction mixture. If desired, external heat can be used after the exothermic heat of reaction terminates. The mixture can then be allowed to cool to ambient temperature and diluted with a suitable inert organic solvent and filtered. The catalyst solids can be washed with additional solvent such as diethylether and the filtrate concentrated by standard means such as a rotary evaporator. The recovered catalyst solids can then be further reused as a hydrosilylation catalyst.

In order that those skilled in the art will be better able to practice the invention, the following examples are given by way of illustration and not by way of limitation. All parts are by weight.

EXAMPLE 1

There was added 100 grams of silica gel from E. Merck and Company, Darmstadt, West Germany, having an average particle size of 40-60 μm particle size was added to a solution of 0.982 grams of γ-mercaptopropyltrimethoxysilane in 500 ml of xylene. The mixture was heated to reflux under a nitrogen atmosphere with mechanical stirring. There was collected 100 ml of solvent as an overhead fraction and 4-5 ml of water. When water ceased to separate from the mixture, it was maintained at reflux (145° C.) with stirring for 16 hours. The mixture was then allowed to cool to ambient temperatures and filtered through a sintered glass funnel under a nitrogen blanket. There was obtained a white powder which was suspended in 400 ml anhydrous methanol and stirred at ambient temperatures. Upon filtering the mixture there was obtained a white powder which was dried under reduced pressure for 16 hours. Based on combustion analysis there was obtained a silica gel having 0.04 m mol of chemically combined mercaptopropylsiloxy, per gram of silica gel.

There was added 5 grams of the above derivatized silica gel to a homogeneous solution of 0.1295 grams of chloroplatinic acid hexahydrate and 50 ml of absolute ethanol. The resulting mixture containing substantially an equal molar amount of platinum atoms and SH was stirred under a nitrogen atmosphere at ambient temperatures for 72 hours. The resulting mixture was then filtered and there was obtained a pale orange filtrate and a pale yellow powder. The pale yellow powder was suspended in 35 ml of ethanol and stirred for 30 minutes. The mixture was then filtered and stored in a glass vial under nitrogen. Based on flame emission analysis, there was obtained a platinum catalyst having about 0.8% by weight of platinum chemically combined to silica gel by platinum-sulfur linkages through mercaptopropylsiloxy groups attached to the silica gel by silicon-oxygen-silicon linkages.

EXAMPLE 2

There was stirred at ambient temperatures a mixture of 11.63 grams of triethylsilane, 10 grams of 1-hexene and 0.084 grams ($8.4 \times 10^{-4}$ Pt/SiH) of the platinum catalyst of Example 1. The mixture was continued for about 10-15 minutes when the temperature peaked at 70° C. External heat was applied and the temperature maintained at 64° C. for 1.5 hours. The mixture was then allowed to cool to ambient temperatures, diluted with 50 ml of hexane and filtered. The residue was washed with 25 ml of ether and the filtrates were concentrated on a rotary evaporator. There was obtained 19 grams of a brown oil representing a yield of 95%. Based on method of preparation and GC and NMR analysis, the product was the linear isomer N-hexyltriethylsilane. The platinum catalyst was obtained as a residue by filtering the reaction mixture. It was washed with diethylether.

The above hydrosilylation procedure was repeated utilizing the recovered platinum substituted silica gel as the hydrosilylation catalyst. Exothermic heat of reaction resulted in a maximum reaction temperature of 40° C. The mixture was then heated to 110° C. for ½ hour. There was recovered 18 grams of product which was a yield of 90%. Based on method of preparation, NMR, and VPC analysis, the product was the linear isomer, n-hexyltriethylsilane.

Three additional hydrosilylation runs were made using the resulting recovered platinum substituted silica gel. It was found that the linear isomer, n-hexyltriethylsilane was formed at 90%, 94% and 90% yield, based on method of preparation, NMR, and VPC analysis. These results established that the platinum substituted silica gel made in accordance with the practice of the present invention was a superior hydrosilylation catalyst which could be readily salvaged and reused several times.

The above hydrosilylation of 1-hexene with triethylsilane was repeated, except that in place of the platinum catalyst of Example 1 there was used an effective amount of a chloroplatinic acid catalyst as shown by Speier, U.S. Pat. No. 2,823,218. The same reaction was repeated, except that a small amount of γ-mercaptopropyltrimethoxysilane was used in the hydrosilylation mixture. It was found that within 10 minutes, the reaction mixture free of the mercaptan started to turn brown and increased in temperature. The exotherm was sufficient to initiate reflux in the 1-hexene mixture. The hydrosilylation mixture containing the mercaptan did not show any change after 15 minutes.

Both hydrosilylation mixtures were then heated to 75° C. After 60 minutes at 75° C. the respective hydrosilylation mixtures were analyzed by gas chromatography. There was obtained a 65% yield of N-hexyltriethylsilane from the mixture free of mercaptan and a 31% yield of N-hexyltriethylsilane from the mixture containing the mercaptan. These results show that sulfur can interfere with a hydrosilylation reaction catalyzed by platinum in particular situations.

EXAMPLE 3

A mixture of 12.495 grams of recrystallized 4-allyloxy-2-hydroxybenzophenone (AHBP), 8.215 grams of triethoxysilane and 0.20 grams of the platinum substituted silica gel of Example 1 was heated at 90° C. It was found that the AHBP melted around 55° C. The reaction mixture became yellow and homogeneous. The temperature of the reaction mixture then quickly rose to 130° C. and then dropped to 90° C. After heating the mixture of an additional hour at about 90° C., the mixture was allowed to cool to 23° C., diluted with 50 ml of hexane and then filtered. The platinum substituted silica gel was recovered as a free-flowing tan powder. The filtrate was concentrated on a rotary evaporator and 20 grams of a yellow oil, a quantitative yield of product was recovered. Based on method of preparation and reverse phase TLC, 4/1;ethanol/water, the product was 4-(3'-triethoxysilylpropoxy)-2-hydroxybenzophenone (SHBP). A trace amowent of 2,4-dihydroxybenzophenone was also obtained. The $^1$H NMR spectrum of the SHBP was found to be identical to a spectrum of SHBP prepared from AHBP and triethoxysilane using a platinum catalyst shown by Karstedt, U.S. Pat. No. 3,775,452.

The above reaction for making SHBP was repeated several times to determine the degree to which the platinum substituted silica gel could be reused. The following results were obtained, where AHBP and SHBP are as previously defined, [SG]—S—Pt is the platinum substituted silica gel of the present invention, THF is tetrahydrofuran, i-BuOH is butanol and MeOH is methanol and h is hour or hours:

TABLE I

| Run # | Catalyst | Solvent | Time | Temp | Yield of SHBP | Recovered AHBP |
|---|---|---|---|---|---|---|
| 2 | from Run #1 | None | 1.2 h | 90° C. | 50% | 50% |
| 3 | from Run #2 | None | 16 h | 100° C. | 85% | 15% |
| 4 | from Run #3 | None | 16 h | 100° C. | 50% | 50% |
| 5 | fresh [SG]—S—Pt | THF 2.5 M | 4 h | 66° C. | 95% | |
| 6 | from Run #5 | THF 2.5 M | 16 h | 66° C. | 90% | |
| 7 | fresh [SG]—S—Pt | i-BuOH 2.5 M | 1.0 h | 60° C. | 95%$^a$ | |
| 8 | fresh [SG]—S—Pt | MeOH 2.5 M | 1.5 h | 60° C. | 50%$^{b,c}$ | |

$^a$Partial exchange of i-butoxy for ethoxy groups at silicon, ca. 33% i-BuO, 66% EtO.
$^a$Partial exchange of methoxy for ethoxy at silicon, ca. 66% MeO, 33% EtO.
$^c$50% Dihydroxybenzophenone was obtained.

The above results show that the platinum substituted silica gel of the present invention can perform as a hydrosilylation catalyst in the presence or absence of an organic solvent. In instances where an organic solvent is used, temperature advantages can be realized. In addition, when the platinum substituted silica gel has been recycled, improved results with respect to yield can be achieved by using the catalyst over longer reaction times.

In order to demonstrate that derivatization of the silica gel with the siloxyorganosulfur groups is necessary to achieve the advantages of the present invention, namely, the ability to reuse the platinum catalyst, the same reaction was repeated for making SHBP from substantially equal molar amounts of AHBP and triethoxysilane, except that a silica gel-platinum catalyst was used which was made from underivatized silica gel. Sufficient chloroplatinic acid hexahydrate was used to provide a loading of 0.05 mm Pt/g silica gel and a catalyst referred to hereinafter as "[SG]—Pt". The [SG]—Pt catalyst was a white powder instead of the white-yellow color of the [SG]—S—Pt catalyst. One possible explanation for the color of the [SG]—Pt catalyst was the platinum was not chemically bound to the underivatized silica gel during catalyst preparation. The hydrosilylation of the AHBP with triethoxysilane using the [SG]—Pt in tetrahydrofuran solvent was conducted and the results obtained are shown in Table II:

TABLE II

| Run # | Catalyst | Solvent | Time | Temp | Yield of SHBP | Recovered AHBP |
|---|---|---|---|---|---|---|
| 1 | fresh [SG]—Pt$^a$ | THF 2.5 M | 72 h | 66° C. | 80% | 15% |
| 2 | from Run #1 | THF 2.5 M | 24 h | 66° C. | 30% | 70% |

$^a$Theoretical, does not assume quantitative binding of Pt to underivatized [SG].

The results in Table II demonstrate the disadvantages of using platinum catalyst which has not been chemically combined to the silica gel substrate in accordance with the practice of the present invention.

EXAMPLE 4

A mixture of 15.306 grams of allyl chloride, 27.09 gram of trichlorosilane and 0.04 grams of [SG]—S—Pt sufficient to provide $1 \times 10^{-5}$ mm Pt/SiH was stirred at 23° C. under a nitrogen atmosphere. The mixture was heated to 60° C. for 16 hours. The mixture was allowed to cool to ambient temperatures and was diluted with 50 ml of hexane and filtered. The filtrate was concentrated on a rotary evaporator to give 33 grams of a clear, colorless oil. Based on method of preparation, NMR and VPC analysis there was obtained about a 92% yield of γ-chloropropyltrichlorosilane and about an 8% yield of n-propyltrichlorosilane.

The platinum catalyst used in the first reaction was used in a second reaction following the same procedure. There was obtained a 70% yield of γ-chloropropyltrichlorosilane and about a 9% yield of n-propyltrichlorosilane.

EXAMPLE 5

There was added dropwise over a period of 30 minutes, 50 grams of allylmethacrylate to a mixture refluxing at 32° C. of 80.6 grams of trichlorosilane and 0.397 grams of a [SG]—S—Pt catalyst sufficient to provide 100 ppm platinum/SiH. The mixture was stirred an additional 2 hours at reflux, cooled to ambient temperature and diluted with 100 ml of hexane and filtered. There was obtained 47.7 grams of a clear, colorless oil upon concentration of the filtrate on a rotary evaporator. Based on method of preparation, NMR and VPC analysis there was obtained a 98% yield of γ-methacryloxypropyltrichlorosilane.

EXAMPLE 6

A mixture of 50 grams of Fisher activity grade 1 alumina having a particle size of 70–170 microns, and 0.49 gram of γ-mercaptopropyltrimethoxysilane was heated to reflux in 300 grams of xylene to effect the removal of water and methanol. The derivatized alumina having chemically combined mercaptopropylsiloxy groups attached to alumina through silicon-oxygen-aluminum linkages, was washed with methanol to remove adsorbed mercaptan and then dried in an oven at 75° C. There was obtained 7.7 grams of derivatized alumina. The derivatized alumina was added to a solution of 0.3 grams of chloroplatinic acid hexahydrate in 45 grams of absolute ethanol. The resulting mixture was stirred under nitrogen for 18 hours. There was isolated a yellow-orange powder after filtration, washing with additional ethanol and drying (70° C., 5 torr) for 2 hours. Based on method of preparation there was obtained a platinum catalyst consisting of platinum atoms attached to an alumina substrate through mercaptopropyl silicon-oxygen-aluminum groups.

There was added 0.4 grams of the above platinum catalyst to a mixture of 11.63 grams of triethylsilane and 10 grams of 1-hexene. Within 5 minutes the color of the mixture had darkened and an exotherm occurred. The mixture was then heated to 75° C. after 0.4 hours. After 1 hour total reaction time a sample of the mixture was withdrawn and analyzed by gas chromatography. There was obtained a 45% yield of N-hexyltriethylsilane.

Although the above examples are directed to only a few of the very many variables which can be utilized in the practice of the method of the present invention, it should be understood that the present invention is directed to a much broader variety of oxides of silicon or aluminum which can be derivatized with alkoxysilylorganomercaptan of formula (1) and thereafter reacted with halogenated platinum compound in accordance with the practice of the present invention as shown by the description preceding these examples as well as the claims below.

What I claim as new and desire to secure by Letters Patent of the United States is:

1. A hydrosilylation method which comprises effecting contact between a silicon hydride and an aliphatically unsaturated organic material in the presence of an effective amount of a platinum catalyst comprising a hydroxylated oxide of silicon or aluminum having a surface area of about 100 to 800 square meters per gram and 0.05% to 5% by weight of chemically combined platinum atoms, which hydroxylated oxide of silicon or aluminum is derivatized with a plurality of

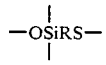

groups attached to the surface hydroxylated oxide of silicon or aluminum by

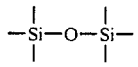

linkages, or

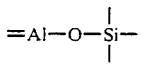

linkages, respectively, and the platinum atoms are chemically combined to the surface of the hydroxylated oxide of silicon or aluminum through the derivatized groups by Pt—S linkages.

2. A method in accordance with claim 1, where the aliphatically unsaturated organic material is 4-allyloxy-2-hydroxybenzophenone.

3. A method in accordance with claim 1, where the silicon hydride is triethoxysilane.

4. A method in accordance with claim 1, where the aliphatically unsaturated organic material is allylchloride.

5. A method in accordance with claim 1, where the silicon hydride is trichlorosilane.

6. A method in accordance with claim 1, where the aliphatically unsaturated organic material is allylmethacrylate.

* * * * *